(12) United States Patent
Speiser

(10) Patent No.: US 10,004,484 B2
(45) Date of Patent: Jun. 26, 2018

(54) THREE LUMEN BALLOON CATHETER APPARATUS

(71) Applicant: Paul Speiser, Vienna (AT)

(72) Inventor: Paul Speiser, Vienna (AT)

( * ) Notice: Subject to any disclaimer, the term of this patent is extended or adjusted under 35 U.S.C. 154(b) by 177 days.

(21) Appl. No.: 14/647,073

(22) PCT Filed: May 30, 2014

(86) PCT No.: PCT/EP2014/061246
§ 371 (c)(1),
(2) Date: May 22, 2015

(87) PCT Pub. No.: WO2014/191549
PCT Pub. Date: Dec. 4, 2014

(65) Prior Publication Data
US 2015/0305725 A1 Oct. 29, 2015

(30) Foreign Application Priority Data

May 29, 2013 (EP) .................................. 13169644

(51) Int. Cl.
*A61B 5/00* (2006.01)
*A61B 10/02* (2006.01)
(Continued)

(52) U.S. Cl.
CPC ...... *A61B 10/0291* (2013.01); *A61B 10/0045* (2013.01); *A61M 5/007* (2013.01);
(Continued)

(58) Field of Classification Search
CPC . A61B 10/0045; A61B 10/02; A61B 10/0291; A61B 2010/0074; A61B 5/3148; A61M 5/007; A61M 5/31511; A61M 25/10; A61M 25/0026
See application file for complete search history.

(56) References Cited

U.S. PATENT DOCUMENTS 4,693,704 A * 9/1987 Ogita ................. A61M 25/1011
604/100.01
5,338,297 A * 8/1994 Kocur ................. A61M 3/0295
604/103.03
(Continued)

FOREIGN PATENT DOCUMENTS

DE 19947907 A1 4/2001
EP 0381042 A1 8/1990
(Continued)

OTHER PUBLICATIONS

Catheters 101: The basic Components of your intermittent catheter—180° Medical website (https://www.180medical.com/blog/post/2014/8/7/catheters-101-the-basic-components-of-your-intermittent-catheter) (downloaded Mar. 21, 2017).
(Continued)

*Primary Examiner* — Max Hindenburg
(74) *Attorney, Agent, or Firm* — Loza & Loza, LLP; Michael Fedrick

(57) ABSTRACT

The present invention relates to a catheter, in particular to a balloon bearing three lumen catheter for dispensing diagnostic fluids into a body cavity and retrieving sample of the diagnostic fluid and a catheter apparatus employing same.

11 Claims, 7 Drawing Sheets

(51) Int. Cl.
*A61M 5/31* (2006.01)
*A61M 25/00* (2006.01)
*A61M 25/10* (2013.01)
*A61B 10/00* (2006.01)
*A61M 5/315* (2006.01)
*A61M 5/00* (2006.01)
*A61M 31/00* (2006.01)

(52) U.S. Cl.
CPC ...... *A61M 5/3148* (2013.01); *A61M 5/31511* (2013.01); *A61M 25/0026* (2013.01); *A61M 25/10* (2013.01); *A61M 31/00* (2013.01); *A61M 2025/1052* (2013.01)

(56) References Cited

U.S. PATENT DOCUMENTS 6,413,228 B1 * 7/2002 Hung ................ A61B 10/0045
435/7.23

8,801,627 B2 * 8/2014 Wiegerinck ........ A61B 10/0096
600/563

2010/0106081 A1 4/2010 Brandeis

FOREIGN PATENT DOCUMENTS

| WO | 03/033045 A2 | 4/2003 |
| WO | 2003/079004 A2 | 7/2006 |
| WO | 2008/058157 A2 | 5/2008 |
| WO | 2013/116816 A1 | 8/2013 |

OTHER PUBLICATIONS

Guimaraes et al., Jornal de Pediatria, 2017, 93(2):172-178 (E-Pub. Jul. 15, 2016).

Ramakrishnan et al., "Urinary Catheters: A Review," The Journal of Family Practice, 2004, 3(2):1-12.

* cited by examiner

Frontal view a)

Top view c)

Section A-A d)

Lateral view b)

Section B-B

Section C-C

THREE LUMEN BALLOON CATHETER APPARATUS

CROSS-REFERENCE TO RELATED APPLICATIONS

This application is the U.S. national stage of International Patent Application No. PCT/EP2014/061246, filed on May 30, 2014 and entitled THREE LUMEN BALLOON CATHETER APPARATUS, which claims the benefit of priority under 35 U.S.C. § 119 from European Patent Application No. 13169644.5, filed May 29, 2013. The disclosures of the foregoing applications are incorporated herein by reference in their entirety.

The present invention relates to a catheter, in particular to a balloon bearing three lumen catheter for simultaneous dispensing diagnostic fluids into a body cavity and retrieving a sample of the diagnostic fluid at the same time and a catheter apparatus employing same.

BACKGROUND OF THE INVENTION

Ovarian cancer is the leading cause of death from gynecologic malignancy in western civilized countries, with an estimated prevalence in Europe and the U.S.A. of 752,600 in 2007 and 59,828 deaths yearly. Treatment and survival of the patients depend primarily on the stage of the disease. Of all ovarian cancer patients only 25% are diagnosed at an early stage while the tumor is confined to the pelvis. In these cases the five-year survival rate is 80% to 90% and the disease can often be cured by the combination of surgery and chemotherapy and are increasingly frequently referred to as type I ovarian cancer. Unfortunately, almost 75% of women affected have advanced stage disease with metastatic spread throughout the abdominal cavity or to retroperitoneal lymph nodes at the time of diagnosis; five-year survival rates fall to 19%-32% for advanced disease, despite maximum surgical effort and combination chemotherapy. This so called type II ovarian cancer is the deadliest cancer in women, even more aggressive than lung cancer.

Diagnostic procedures which require a non-surgical entry into the uterus are well known. One such procedure known as hysterosalpingography is a radiographic method for imaging the anatomical structures of the uterus and fallopian tubes.

Hysterosalpingography involves inserting a fine flexible catheter through the cervical canal and injecting a contrast medium, such as an iodinated fluid, into the uterus. Radiography is then carried out to provide imaging information pertaining to the subject uterus.

Another well-known diagnostic procedure which entails the non-surgical entry into the uterus is called saline contrast hysterosonography. This procedure also employs a fine flexible catheter that is inserted into the cervical canal of the uterus. The catheter in this procedure enables the physician or technician to inject a sterile saline solution into the uterus to expand it so that an ultrasound scanner can be used to sonographically observe the uterus.

The uterine cavity is in a sense a virtual space, because the anterior and posterior walls of the uterus are in direct contact to each other. Particularly in postmenopausal but also in non-pregnant premenopausal women the body of uterus containing the uterine cavity is very small. The cavity itself has a triangular shape measuring only app. 3 cm in length and app. 2 cm at the roof. When a fluid gets dispensed into the cavity, it immediately evacuates through the fallopian tubes into the peritoneal cavity and the dispensed fluid cannot be retrieved anymore. Furthermore on aspiration the opening of catheters tend to get obstructed by loose tissue from the lining of the cavity called endometrium or by blood clots frequently present in the uterine cavity.

Cells shed from the lining of the fallopian tube and ovary get transported into the cavity and are of great interest for detecting premalignant and malignant changes in these tissues. These cells are extremely little in number making it difficult to sample them. All sampling devices for the uterine cavity to date are designed to sample tissue of the lining of the uterine cavity to detect premalignant or malignant changes of the endometrium. For the detection of the minute number of cells shed from the lining of the fallopian tube and ovaries and that found their way into the uterine cavity a sampling device is desired that would allow retrieving those loose cells with as little as possible contamination of endometrial tissue.

To overcome these problems a catheter is desired that has a very short tip to fit into the small space of the uterine cavity, that allows for simultaneous flushing of fluid into the uterine cavity and proximal tubes and aspirating the fluid at the same time, preventing the fluid to evacuate through the fallopian tubes. To reduce the risk of obstruction the channels should have more than one opening ideally pointing into different directions. To prevent the fluid from back flowing through the cervical canal, a small balloon would be desirable.

WO03033045 discloses a catheter with suction capability to obtain a biosample. Specifically, the catheter is designed for collecting prostatic fluid from the prostatic urethra and/or the membranous urethra. To obtain a biosample, the catheter exhibits biosample entry ports (25) which are positioned along the elongated body. Additionally the catheter has a urinary drainage port (26). Therefore, the catheter according to WO03033045 is not suitable to simultaneously dispense a diagnostic fluid and retrieve a sample of the dispensed fluid at once.

PCT/EP2013/051899 discloses a non-invasive method for the diagnosis of adenocarcinoma or their precursor lesions of ovaries, fallopian tubes and endometrial lining in a female subject by analyzing cells of said subject wherein a uterine catheter designed for non-invasive rinsing of the uterine cavity and collecting a sample of the rinse.

One problem associated with said catheters of this design is that they have a closed tip which makes it difficult to retrieve a sample of the dispensed fluid, representing a lavage of the fallopian tubes and uterus. Therefore, a catheter which allows for simple and reproducible retrieving a sample from the dispensed fluid is desirable.

SUMMARY OF THE INVENTION

It is an aspect of the invention to provide an improved catheter which can be used for non-surgical entry into a uterus to dispense a diagnostic fluid therein and to retrieve a sample of the dispensed fluid simultaneously representing a lavage of the fallopian tubes and uterus. The catheter comprises an elongated body having two single lumens extending continuously from a proximal end up to the top of the tip at the distal end and a third lumen extending continuously from the proximal end to an inflatable balloon.

DETAILED DESCRIPTION OF THE INVENTION

Figure 1A:
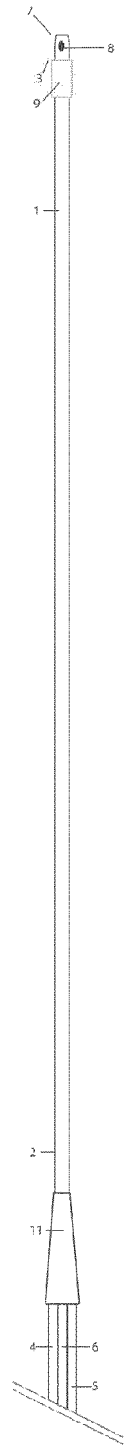
FIGS. 1*a* and 1*b* are a view of the catheter.

The present invention relates to a catheter useful for non-surgical entry into a uterus to dispense a diagnostic fluid therein and to retrieve simultaneously a sample from said dispensed fluid representing a lavage of the fallopian tubes and uterus, the catheter comprises:

an elongated body (1) having three lumens (4, 5 and 6), a balloon (9) disposed marginally adjacent to the distal end (3) of the elongated body (1) for fluid sealing the interior of the subject's uterus; wherein lumens (4 and 5) extend from the proximal end (2) up to the distal end (3) of the elongated body, and lumen (6) extends from the proximal end (2) to the distal end (3) with an opening that lies proximally from the distal end (3) for inflating the balloon (9), and lumen (4) has an opening (4') at the top of the tip for dispensing a diagnostic fluid into the interior of a subject's uterus and tubes, and lumen (5) has an opening (5') at the top of the tip for retrieving a sample of said dispensed fluid of the interior of a subject's uterus representing a lavage of the fallopian tubes and uterus simultaneously.

An embodiment of the invention is the catheter as described above, wherein the lumens (4 and 5) have additionally side openings (8) between the top of the tip and the balloon.

A further embodiment of the invention is the catheter as described above, wherein the lumens (4 and 5) have connecting means for connecting syringes.

A further embodiment of the invention is the catheter as described above, wherein the third lumen has a closure device (10) at the proximal end (2) for closing the lumen upon filling the balloon with said closure device at the proximal end.

A further embodiment of the invention is the catheter as described above, wherein said closure device (10) is a blocking valve.

A further embodiment of the invention is a kit for dispensing a diagnostic fluid and to retrieve a sample from the dispensed fluid from a subject's uterus, comprising a catheter as described above, an application assembly for connecting two syringes; and an adapter for simultaneously moving the two plungers in opposite directions.

A further embodiment of the invention is the kit as described above, wherein said adapter has a lip (19).

A further embodiment of the invention is the use of a kit as described above for screening a female population being at risk of endometrial cancer or suffering from premalignant changes of the endometrium or endometrial cancer.

A further embodiment of the invention is the use of a kit as described above for screening a female population being at risk of ovarian cancer or suffering from premalignant changes of the ovary or ovarian cancer.

A further embodiment of the invention is the use of a kit as described above for screening a female population being at risk of cancer of the fallopian tube or suffering from premalignant changes of the tube or tubal cancer.

A further embodiment of the invention is a non-invasive method of collecting a sample for ex vivo diagnostic purposes by rinsing the uterine cavity and optionally the fallopian tubes of a subject with a lavage fluid and retrieving a cell sample from the rinse.

The invention is now described by reference to various specific embodiments which are shown in the attached drawings. It is to be clearly understood that these embodiments are shown for purpose of illustration only and are not limiting.

Figure 1B:
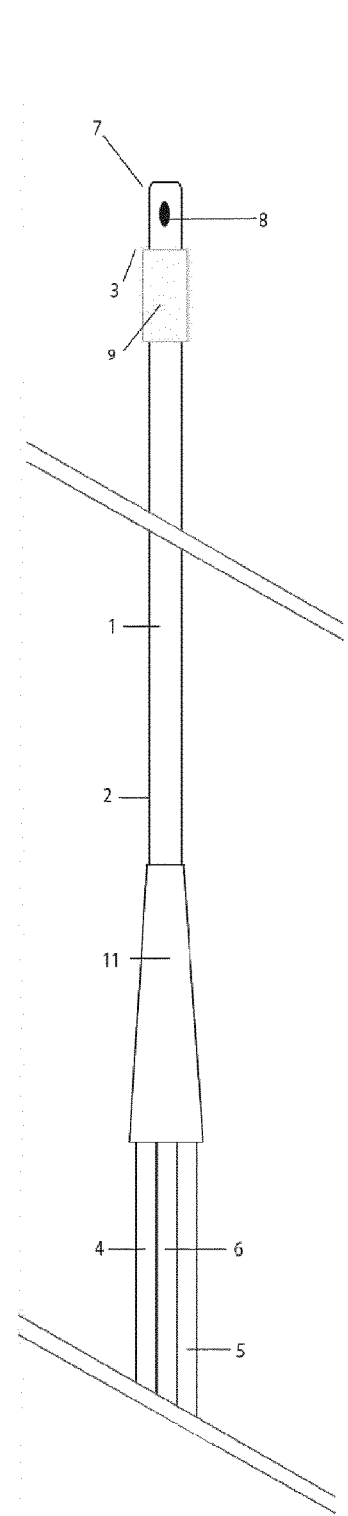

Attention is first directed to FIGS. 1a and 1b, which show a catheter with an elongated body (1) and three internal lumens (4, 5 and 6). Two lumens (4 and 5) extend to the distal end of the elongated body (1) with openings (4' and 5') at the top of the tip at the distal end. "Distal end" refers to the end furthest from the person holding the apparatus, and "proximal end" refers to the end closest to the holder of the apparatus. Optionally the lumens (4 and 5) have side openings (8) adjacent to the tip of the catheter. The additional side openings (8) are located close to the tip of the catheter, in particular between the tip of the catheter and the balloon.

The third lumen (6) ends relatively close to the distal end of the elongated body (1) where the balloon is disposed and communicates through the bore with the interior of the balloon (9).

The balloon is adjacent to the tip of the catheter and seals the cervix which is a prerequisite to obtain a sample of the lavage solution. The balloon is made of expandable material. When deflated, the balloon (9) lies closely adjacent to the body, so as not to interfere with the insertion or withdrawal of the catheter. When the balloon is inflated by providing e.g. normal saline through the lumen (6) it seals the cervical canal.

It is further required, that the elongated body does not contain any additional openings between the balloon and the proximal end of the elongated body (1). Additional openings between the balloon and the proximal end of the elongated body would be conflicting with the aim of the invention to lavage the uterus and to obtain a sample of the lavage fluid at the same time.

Figure 2:
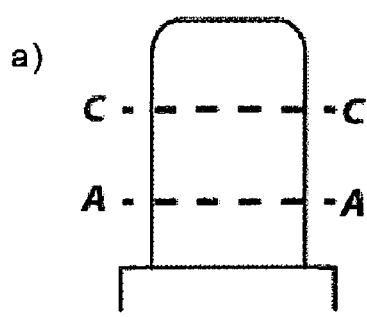
FIGS. 2*a, b, c,* and *d* are detailed sections of the tip.
Figure 2:
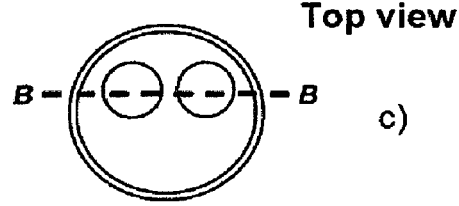
Figure 2:
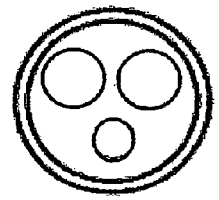
Figure 2:
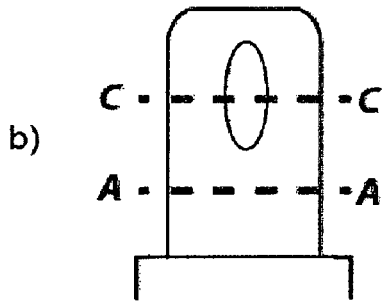
Figure 2:
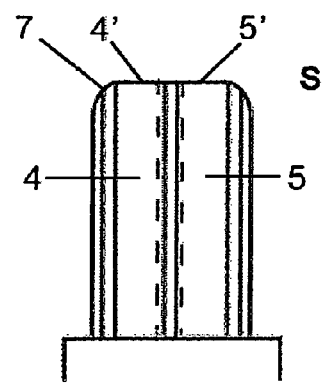
Figure 2:
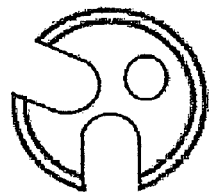

FIG. 2 shows frontal view (a) and lateral view (b), top view (c) and sections (A-A, B-B, C-C) (d) of the tip. Section B-B exhibits the two openings (4' and 5') of lumens (4 and 5) on the top of the tip (7). Section A-A exhibits the three lumens (4, 5 and 6) within in the elongated body (1).

Figure 3:
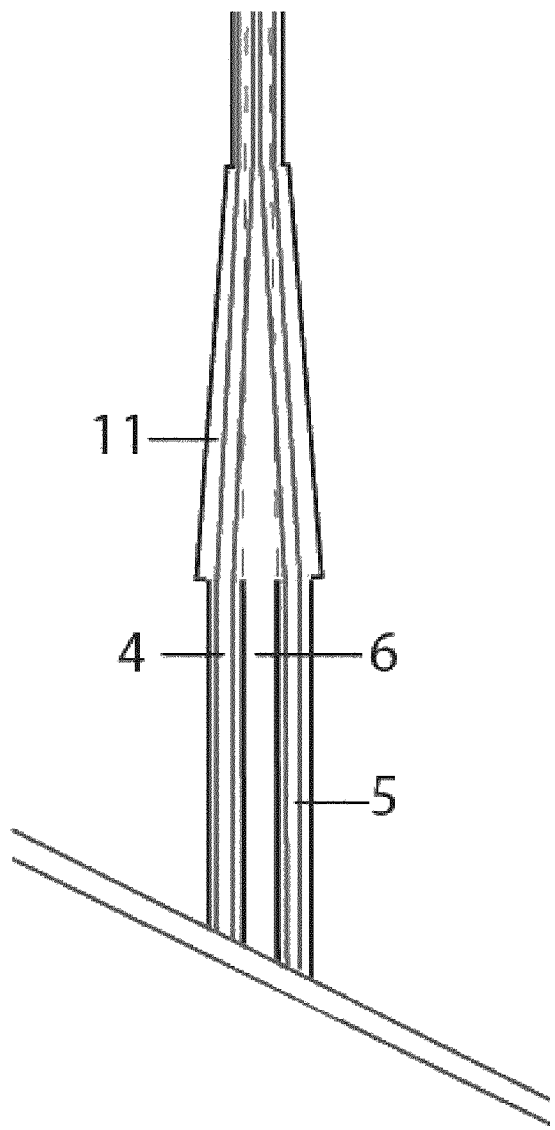
FIG. 3 is a view of the connecting element.

FIG. 3 shows a connecting element (11) at the proximal end (2) of the elongated body (1) in which the lumens (4, 5 and 6) are fixed.

Figure 4:
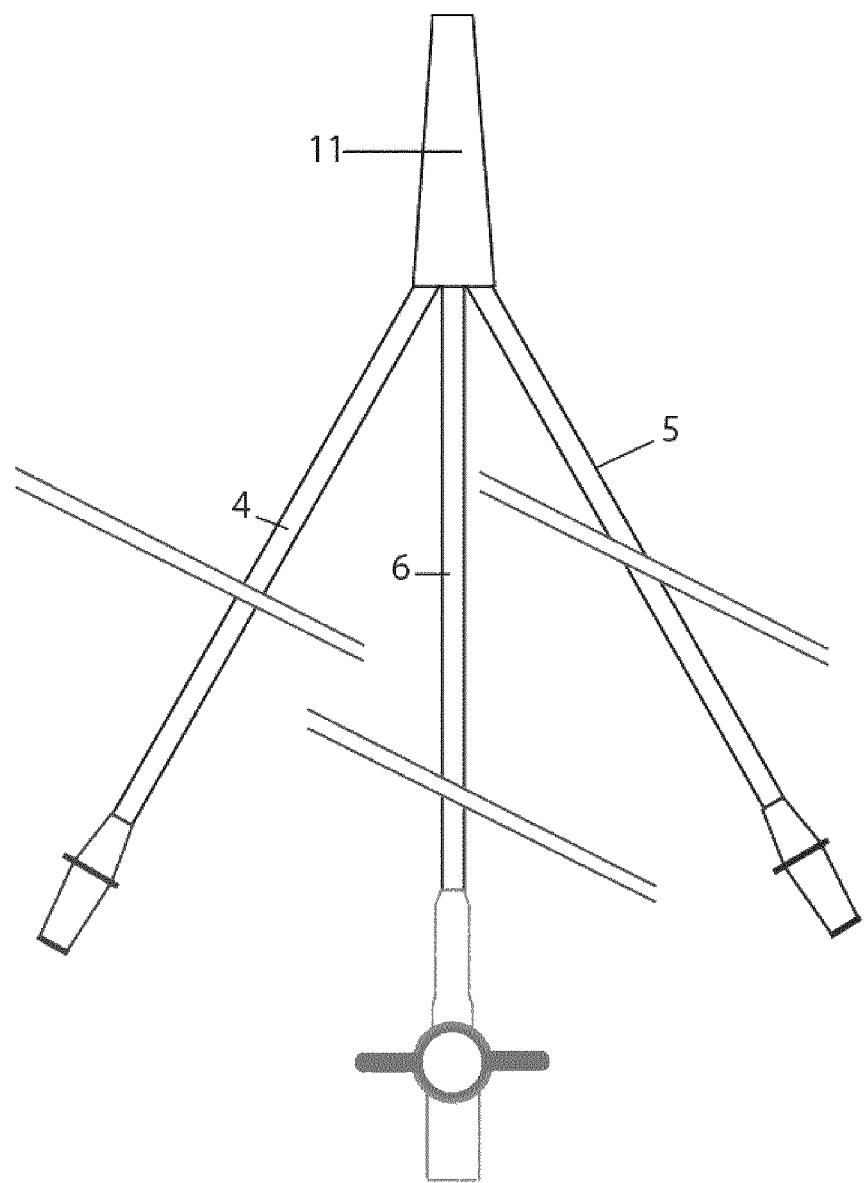
FIG. 4 is a view of the proximal end of the catheter.

FIG. 4 shows the proximal end of the catheter, wherein the three lumens are extending the connecting element (11). The lumens (4 and 5) may be connected to syringes. The lumen (6) may bear a closing element, such as for example a blocking valve or a plug. The connection is normally made by supplying small coupling elements to connect the lumens to the syringes.

Figure 5:
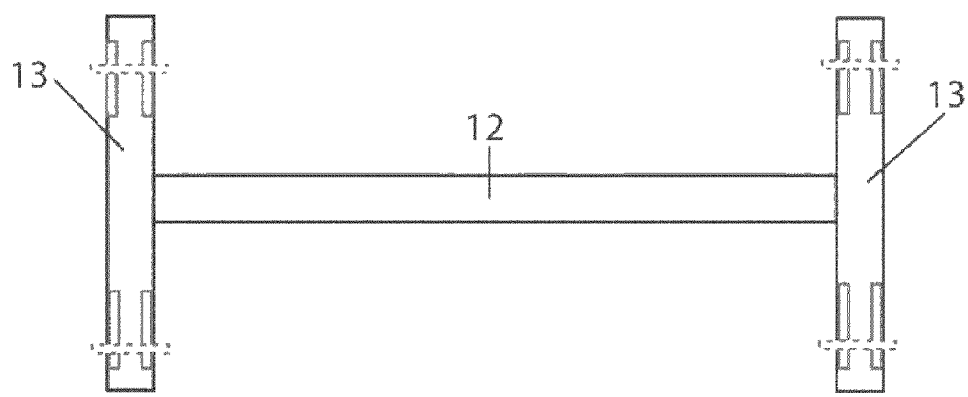
FIG. 5 is a view of an applicator assembly.

FIG. 5 shows an applicator assembly for connecting two syringes. The applicator assembly consists of at least one guide bar (12) and two ports (13). In the ports (13) the flanges 16 and 17 of the syringes are affixed.

Figure 6:
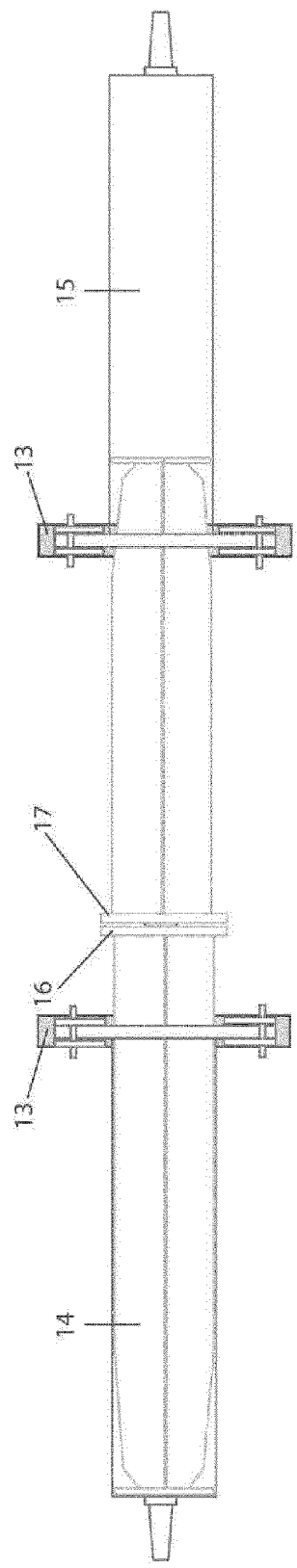
FIG. 6 is a view of two syringes fixed in the applicator assembly.

FIG. 6 shows two syringes (14) and (15) affixed in the applicator assembly. One syringe (14) is empty, thus the plunger is in the zero position. The other syringe (15) is filled with a lavage fluid, for example with normal saline.

Figure 7:
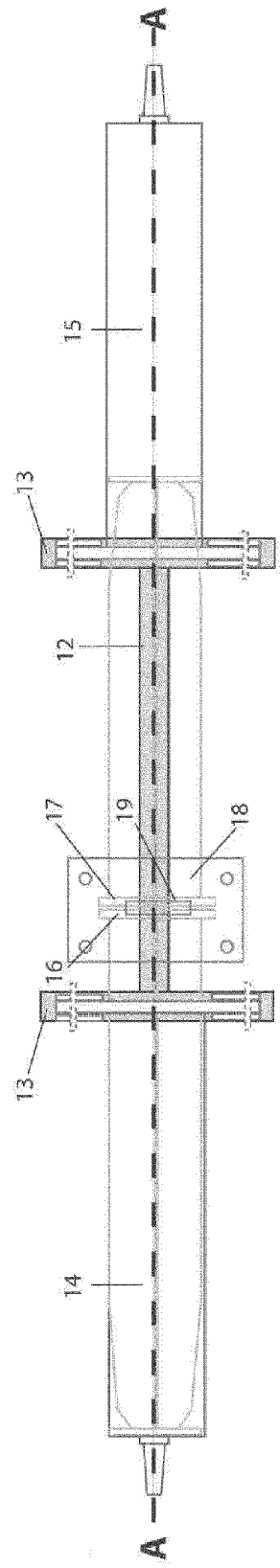
FIG. 7 is a view of the applicator assembly with an adapter.

FIG. 7 shows the applicator assembly with an adapter 18 for connecting the flanges 16 and 17 of the syringes (14) and (15).

Figure 8:
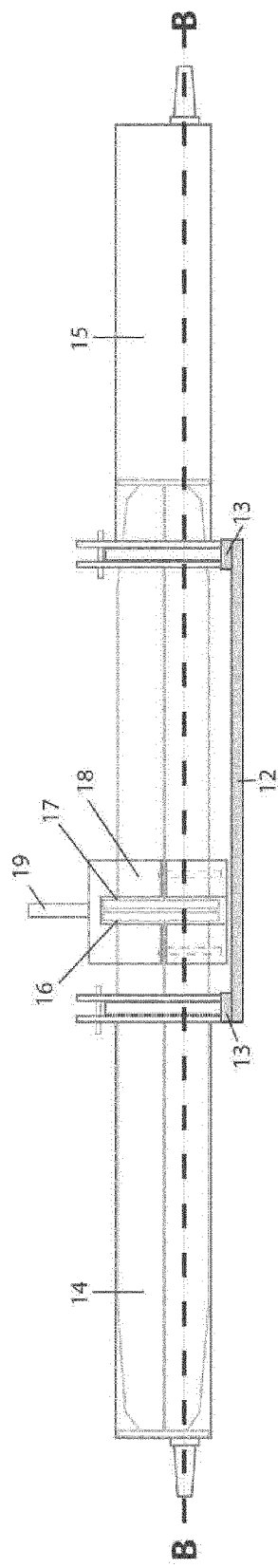
FIG. 8 is a view of applicator assembly with the adapter and a lip.

FIG. 8 shows the applicator assembly with the adapter 18, wherein the adapter has a lip (19) which allows for the application of the lavage fluid. Upon dispensing the lavage fluid, the plunger of syringe (15) is moved to the zero position and the plunger of syringe (14) is pulled back. By pushing on the plunger of the lavage fluid containing syringe, the fluid is slowly syringed into the uterine cavity and tubes. Simultaneously the plunger of the empty syringe is gently pulled out, sucking the fluid from the uterine cavity and tubes. While one tube slowly empties, the other slowly fills up. Thus, the adapter 18 with the lip (19) allows for simultaneous rinsing and sucking.

According to a specific example, two 10 ml syringes—one of them containing 10 ml of normal saline—are connected to the two lumens (4 and 5). By pushing on the lip (19) the normal saline containing syringe (15), the fluid is slowly syringed into the uterine cavity and tubes. Simultaneously the plunger of the empty syringe (14) is gently pulled out, sucking the fluid from the uterine cavity and tubes. While one tube slowly empties, the other slowly fills up. After the lavage is finished, a cap is put on the filled syringe and the syringe is sent into the laboratory for diagnosis.

The catheters used in this procedure typically have means for sealing off the uterus before or during injection of the fluid to prevent backflow into the vagina. One such means includes an inflatable intrauterine balloon made from an elastomeric material which is disposed adjacent the distal tip of the catheter.

The balloon catheter is operated by inserting the distal tip thereof through the cervical canal and into the uterus with the intrauterine balloon deflated. The insertion of the distal tip operates to position the deflated intrauterine balloon in the uterus or cervical canal. Once positioned, the inflation syringe is used to inflate the balloon with air or saline to create a seal in the cervical canal and the injection syringe is used to inject the desired diagnostic fluid into the uterus.

The uterus and the fallopian tubes are rinsed with the diagnostic fluid. Due to the specific design of the catheter, a sample of said diagnostic fluid could be obtained at the same time which is useful for further analysis.

The development of an alternate and new test to detect ovarian cancer or tubal cancer or endometrial cancer and their precursor lesions is imperative, in particular serous ovarian cancer or tubal cancer or endometrial cancer or disease of early stages. Thus, the present invention is a valuable contribution to a convenient, safe and cost-effective test possibly used for early diagnosis or in a screening program looking for cancer or precancerous lesions in women who have no symptoms of the disease.

The invention claimed is:

1. A catheter useful for non-surgical entry into a subject's uterus to dispense a diagnostic fluid therein and to the fallopian tubes and to retrieve a sample from said dispensed fluid, the catheter comprising:

an elongated body having a proximal end, a distal end, a first lumen, a second lumen, and a third lumen,
a balloon disposed marginally adjacent to the distal end of the elongated body for fluid sealing the interior of the subject's uterus;
wherein the first and second lumens extend from the proximal end up to the distal end of the elongated body and the third lumen extends from the proximal end to a point before the distal end and has an opening proximal to the distal end to inflate the balloon,
wherein the first lumen has first distal opening at a distal tip of the distal end of the catheter for dispensing a diagnostic fluid into the interior of the subject's uterus, wherein the first distal opening is longitudinal to the axis of the first lumen, and
wherein the second lumen has second distal opening at the distal tip of the distal end of the catheter for retrieving a sample of said dispensed fluid from the interior of the subject's uterus, wherein the second distal opening is longitudinal to the axis of the second lumen.

2. The catheter according to claim 1, wherein the elongated body is devoid of additional openings.

3. The catheter according to claim 1, wherein the first and second lumens have additional side openings between the tip and the balloon.

4. The catheter according to claim 1, wherein the first and second lumens have connecting means for connecting syringes.

5. The catheter according to claim 1, wherein the third lumen has a closure device at the proximal end for closing the third lumen upon filling the balloon with said closure device at the proximal end.

6. The catheter according to claim 5, wherein said closure device is a blocking valve.

7. A kit for dispensing a diagnostic fluid and for retrieving a sample from said dispensed fluid from a subject's uterus and fallopian tubes, comprising:
a catheter according to claim 1,
an application assembly for connecting two syringes to the catheter, wherein each syringe comprises a plunger; and
an adapter for simultaneously moving the two plungers of said syringes in opposite directions.

8. The kit according to claim 7, wherein said adapter has a lip.

9. A non-invasive method of collecting a sample for ex vivo diagnostic purposes, comprising the steps of:
providing the kit of claim 7;
rinsing the uterine cavity and fallopian tubes of a subject with a lavage fluid, thereby creating a rinse; and
retrieving a cell sample from the rinse.

10. The method of claim 9, further comprising the step of selecting a subject at risk of contracting a cancer selected from the group consisting of endometrial cancer, ovarian cancer, and tubal cancer.

11. The method of claim 9, further comprising the step of detecting premalignant changes of a cell from the endometrium, ovaries, or fallopian tubes.

* * * * *